United States Patent
Zerbato (10) Patent No.: US 10,112,296 B2
(45) Date of Patent: Oct. 30, 2018

(54) REMOTE MANIPULATION INPUT DEVICE

(71) Applicant: BBZ, S.R.L., Vigasio (VR) (IT)

(72) Inventor: Davide Zerbato, Lavagno (IT)

(73) Assignee: BBZ S.R.L., Vigasio (VR) (IT)

( * ) Notice: Subject to any disclaimer, the term of this patent is extended or adjusted under 35 U.S.C. 154(b) by 96 days.

(21) Appl. No.: 15/328,442

(22) PCT Filed: Jun. 30, 2015

(86) PCT No.: PCT/IB2015/054921
§ 371 (c)(1),
(2) Date: Jan. 23, 2017

(87) PCT Pub. No.: WO2016/020773
PCT Pub. Date: Feb. 11, 2016

(65) Prior Publication Data
US 2017/0210005 A1    Jul. 27, 2017

(30) Foreign Application Priority Data

Aug. 8, 2014 (IT) ................ VI2014A0211

(51) Int. Cl.
*B25J 9/16* (2006.01)
*B25J 3/04* (2006.01)
(Continued)

(52) U.S. Cl.
CPC ............ *B25J 9/1612* (2013.01); *A61B 34/37* (2016.02); *A61B 34/74* (2016.02); *B25J 3/04* (2013.01);
(Continued)

(58) Field of Classification Search
CPC .. B25J 9/1612; B25J 3/04; B25J 13/02; A61B 34/37; A61B 34/74; A61B 2034/741; G09B 9/00; H01F 7/0205
See application file for complete search history.

(56) References Cited

U.S. PATENT DOCUMENTS 5,784,542 A * 7/1998 Ohm .......................... B25J 3/04
                                                     700/247
5,876,325 A * 3/1999 Mizuno .............. A61B 1/00048
                                                     600/102
(Continued)

FOREIGN PATENT DOCUMENTS

WO      2012/153152 A1    11/2012

OTHER PUBLICATIONS

International Search Report and Written Opinion dated Nov. 10, 2015, issued in PCT Application No. PCT/IB2015/054921, filed Jun. 30, 2015.

*Primary Examiner* — Thomas C Diaz
(74) *Attorney, Agent, or Firm* — Workman Nydegger (57) ABSTRACT

A multidimensional input device includes an anthropomorphic arm with a handpiece which can be grasped by an operator configured to interact with a scenario represented in a display unit. The handpiece is removably associable to the terminal section of the anthropomorphic arm through a magnetic coupling spherical joint and includes: an inertial platform having an accelerometer, a gyroscope and a magnetometer; a gripper provided for the operator. The spherical joint has a spherical head belonging to the terminal section of the anthropomorphic arm or the handpiece, the spherical head being configured to be removable coupled to a corresponding spherical seat belonging to the handpiece or the terminal section of the anthropomorphic arm. The spherical head and/or the spherical seat are magnetized.

9 Claims, 6 Drawing Sheets

(51) Int. Cl.
 *B25J 13/02* (2006.01)
 *A61B 34/37* (2016.01)
 *A61B 34/00* (2016.01)
 *G09B 9/00* (2006.01)
 *H01F 7/02* (2006.01)

(52) U.S. Cl.
 CPC ............... *B25J 13/02* (2013.01); *G09B 9/00* (2013.01); *H01F 7/0205* (2013.01)

(56) References Cited

U.S. PATENT DOCUMENTS

| | | |
|---|---|---|
| 6,919,787 B1 | 7/2005 | Macken |
| 9,232,980 B2 * | 1/2016 | Kishi .................. A61B 19/2203 |
| 2003/0146898 A1 | 8/2003 | Kawasaki et al. |

* cited by examiner

REMOTE MANIPULATION INPUT DEVICE

BACKGROUND OF THE INVENTION

1. Field of the Invention

The invention regards a multidimensional input device configured to interact with a scenario represented in a display unit and used for the remote manipulation of real or virtual apparatus.

2. Present State of the Art

The device of the invention is particularly useful in the use for simulating the use of surgical instruments.

However, it should be observed that the device of the invention may be used in any remote manipulation situation.

As known, in the market there are available devices used for interacting with a display unit for performing remote manipulation operations.

Such devices essentially comprise a processing unit to which there is connected a monitor on which there is displayed a scenario with which the operator interacts utilizing an input device.

The scenario that is displayed may represent, for example, objects to be taken and moved from one point to another and the operator interacts with such scenario manoeuvring the aforementioned input device which, generally, comprises a handpiece associated to an articulated arm of the anthropomorphic type.

According to the prior art, the handpiece is connected to the terminal part of the anthropomorphic arm through mechanical joining means which simulate the movement of a wrist.

The user has several handpieces, each of which simulates the use of a different tool or instrument, and such handpieces should be replaceable in a quick and easy manner.

However, the mechanical joining means of the known type reveal the drawback of not allowing the quick replacement of the handpieces and this increases the simulation times, especially when the simulations require the replacement of several handpieces.

In addition, the movements of the handpiece according to the three opposite Cartesian axes at the joint which simulates the wrist are controlled by sensors housed in the wrist and thus upstream of the handpiece.

This implies a further executive complication in the obtainment of the anthropomorphic joint between the arm and handpiece at the wrist.

Patent document US 2003/0146898 which describes a handpiece associated to an anthropomorphic arm through a magnetic coupling spherical joint which makes the connection and separation of the handpiece by the anthropomorphic arm easy and quick is known.

Patent document WO 2012/153152 which describes a handpiece having the shape of a robotic surgical instrument, to which sensors adapted to measure the acceleration and the angular movement of the handpiece as well as the magnetic field around the handpiece are associated is also known.

SUMMARY OF THE INVENTION

The present invention intends to overcome the aforementioned drawbacks.

In particular, the first object of the invention is to provide a multidimensional input device comprising a handpiece having greater manoeuvrability with respect to the handpieces of equivalent devices of the prior art.

Another object of the invention lies in the fact that the handpiece can be replaced more easily with respect to the handpieces of equivalent devices of the prior art.

Last but not least, an object of the invention lies in the fact that the handpiece contains the sensors for detecting the movements of the handpiece according to the three opposite Cartesian axes in the joint which simulates the wrist of the handpiece.

The objects listed above are attained by a multidimensional input device having the characteristics according to the main claim to which reference shall be made.

Other characteristics of the device of the invention are described in the dependent claims.

Advantageously, the device of the invention, considering the greater manoeuvrability of the handpiece and the fact that it is easier to replace, quickens the operations of interaction with the scenario represented in a display unit, with respect to the use of equivalent devices of the prior art.

BRIEF DESCRIPTION OF THE DRAWINGS

The aforementioned objects and advantages shall be outlined in the description of a preferred embodiment of the device of the invention provided hereinafter with reference to the attached drawings, wherein.

DETAILED DESCRIPTION OF THE PREFERRED EMBODIMENTS

Figure 1:
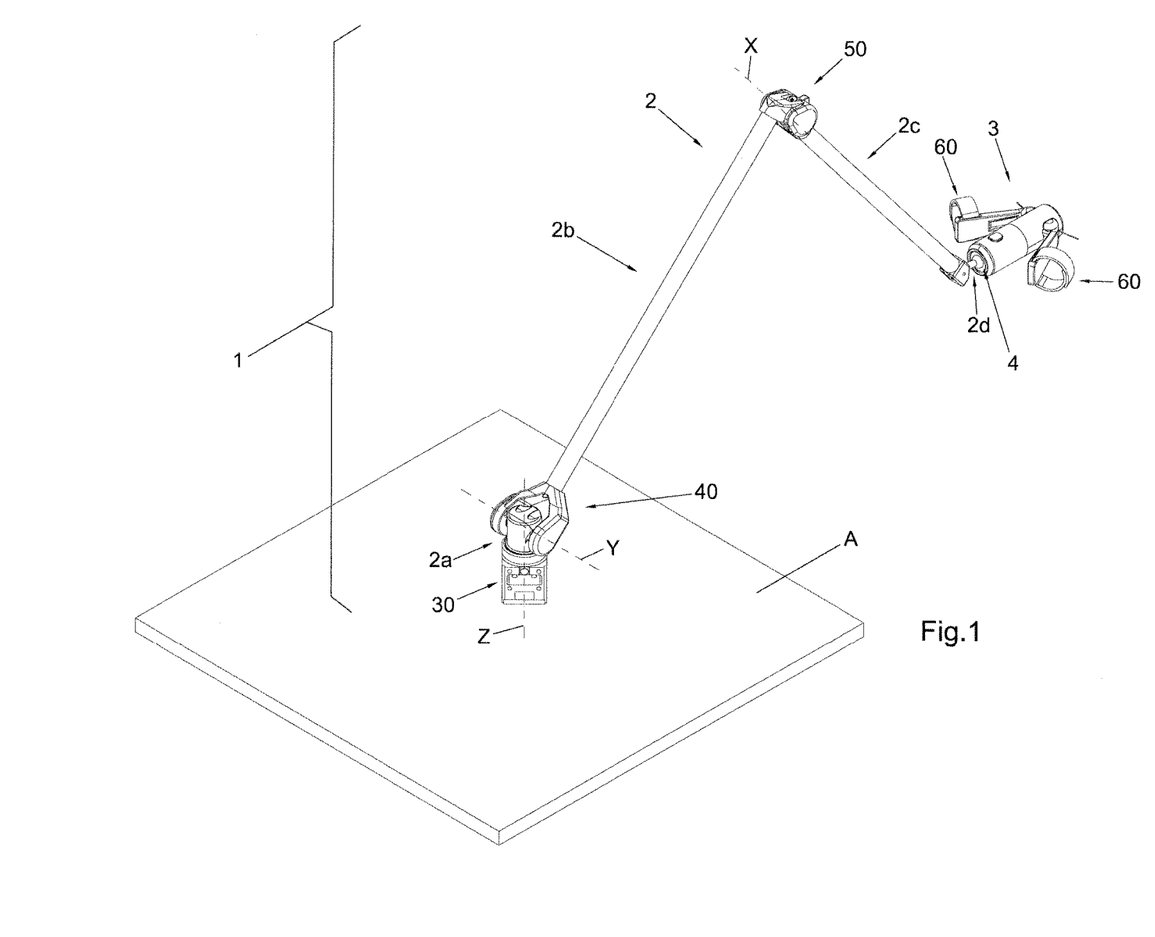
FIG. 1 represents the device of the invention in axonometric view.
Figure 2:
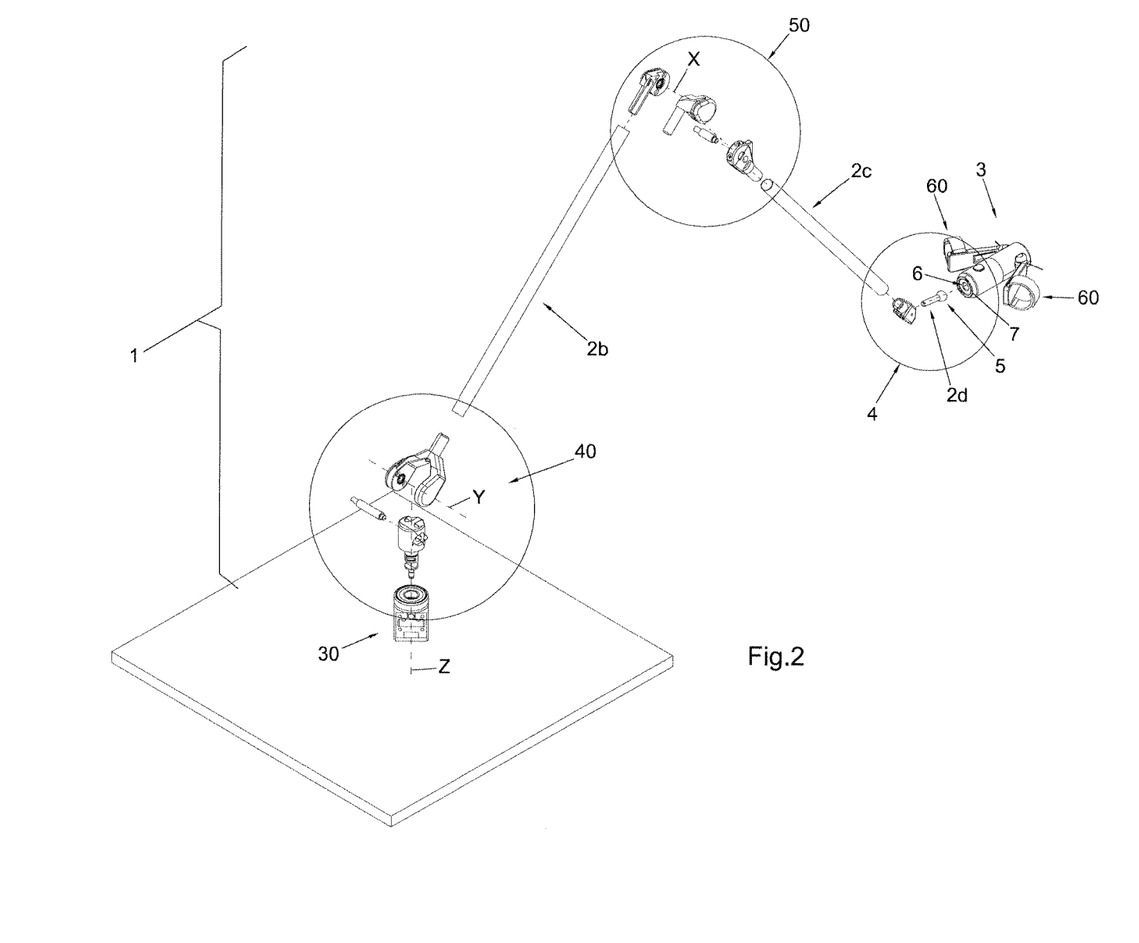
FIG. 2 represents the device of FIG. 1 partially exploded.
Figures 3, 4, 5:
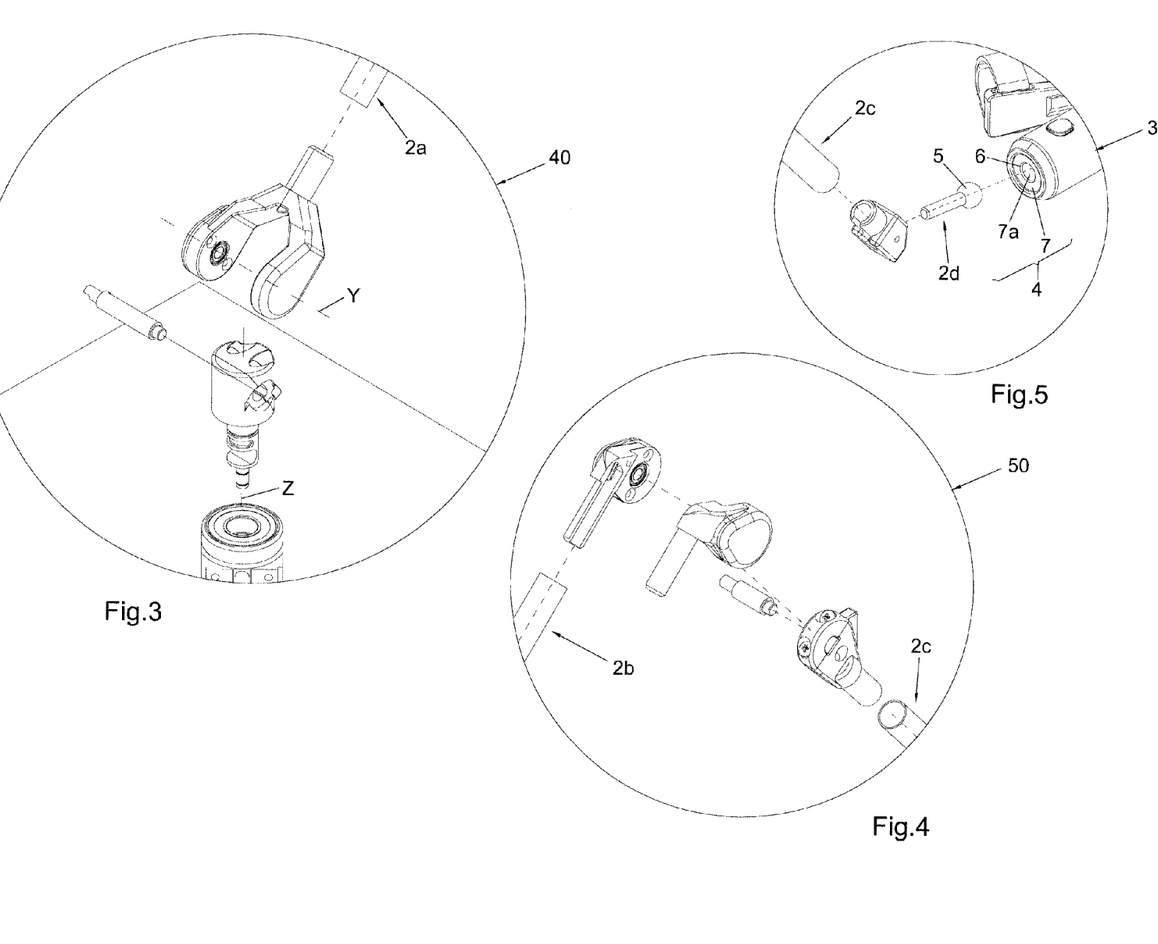
FIGS. 3 to 5 represent enlarged details of FIG. 2.

The input multidimensional device object of the invention is represented in axonometric view in FIGS. 1 and 2 where it is indicated in its entirety with 1. It should be observed that it comprises an anthropomorphic arm 2 with a handpiece 3 which can be grasped by an operator configured to interact with a scenario represented in a display unit, said scenario and said display unit not being represented with drawings for the sake of executive simplicity of the drawings themselves.

The display unit is constituted by a monitor of the known type on which the scenario subject of display may be a virtual scenario, should the multidimensional input device of the invention be used for teaching and training purposes, or a real scenario, should the device be used for the remote control of a robot arranged in remote position.

As regards the anthropomorphic arm 2 it should be observed that it comprises: a first section 2a which is associated to a support structure A through a first joint 30 configured to define a first rotation axis Z and a second section 2b which is associated to the first section 2a through a second joint 40 configured to define a second rotation axis Y.

The anthropomorphic arm 2 also comprises a third section 2c associated to the second section 2b through a third joint 50 configured to define a third rotation axis X and a terminal section 2d having an end configured to be associated to the third section 2c and the opposite end associated to the handpiece 3 according to a configuration which defines a spherical joint 4 to be better defined hereinafter.

Thus, the first joint 30 is referred to as "torso joint", the second joint 40 is referred to as "shoulder joint", the third joint 50 is referred to as "elbow joint" and the spherical joint 4 is referred to as a "wrist" according to a denomination of the anthropomorphic type which identifies the method of movement of the handpiece 3 associated to the anthropomorphic arm 2.

According to the invention, the handpiece 3 is removably associable to the terminal section 2d of the anthropomorphic arm 2 through the spherical joint 4 which is of the magnetic coupling type.

As regards the magnetic coupling spherical joint 4 it is observed that, in particular in FIGS. 2 to 10, it comprises a spherical head 5 belonging to the terminal section 2d of the anthropomorphic arm 2, which is configured to be removably coupled to a spherical seat 6 which belongs to the handpiece 3.

In particular, it is observed that the spherical seat 6 belongs to an annular body 7 which is associated to the handpiece 3 and in which the spherical seat 6 is constituted by the perimeter edge which delimits the through hole 7a obtained in the annular body 7.

It is clear that in a different embodiment the spherical head 5 may belong to the handpiece 3 and it may be configured to be removably coupled to a corresponding spherical seat 6 belonging to the terminal section 2d of the anthropomorphic arm 2.

In other embodiments the spherical head 5 may be magnetised instead of the spherical seat 6, or both may be magnetised with different polarities.

Figure 9:
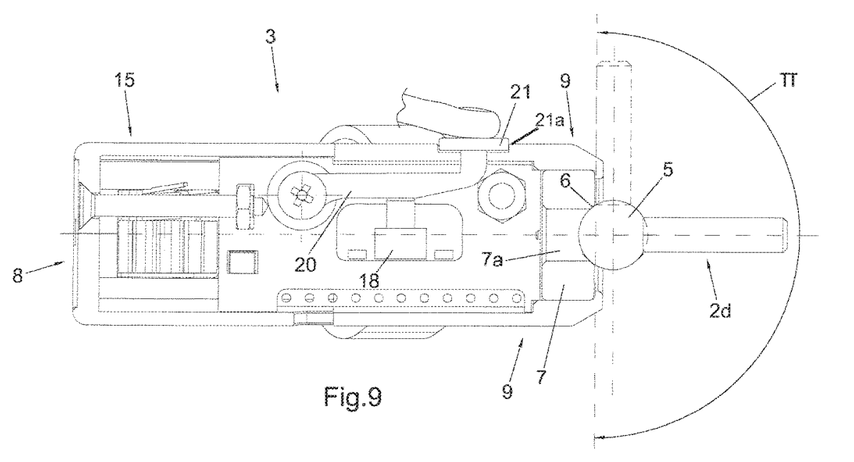
FIGS. 9 and 10 represent two longitudinal sections of the detail of FIG. 8 in two different operating positions.
Figure 10:
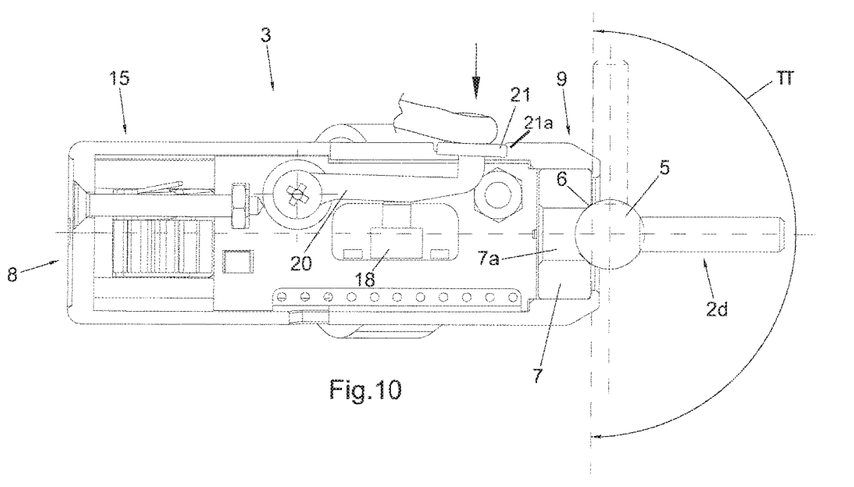

Regardless of the fact that the spherical joint is obtained according to one or the other described embodiments, it allows obtaining both objects set by the invention given that, the coupling between the spherical head 5 and the spherical seat 6 being of the magnetic type, a quick coupling and de-coupling of the handpiece 3 from the anthropomorphic arm 2 is opposable without having to proceed long and laborious operations for mounting and demounting the coupling spherical joint which are instead necessary in equivalent devices of the known type available in the market; given that the spherical seat 6 is constituted by the perimeter edge which delimits the through hole 7a from the annular body 7, the spherical seat 6 which is only coupled with one part of the surface of the spherical head 5 and this allows the mutual rotation of the handpiece 3 with respect to the terminal section 2d of the anthropomorphic arm 2 according to a solid angle whose width may reach the value π, as observable in FIGS. 9 and 10.

Configurations in which, suitably comparing the diameter of the terminal section 2d with the diameter of the spherical head 5, it is possible to obtain rotations according to solid angles with width even greater than the value π are also possible.

As regards the handpiece 3 it is observed—particularly in FIGS. 6 to 10—that it comprises a first end 8 configured to be faced towards the user and a second end 9, arranged on the opposite side, configured to receive the annular body 7. In the handpiece 3 there is present a framework 17 configured for supporting an inertial platform which comprises an accelerometer 11, a gyroscope 12 and a magnetometer 13.

In addition, a gripper 14 provided for the operator, whose opening is measured by the magnetometer 13, as described hereinafter in detail, is also part of the handpiece 3.

The handpiece 3 is also defined by a modular casing 15 in which there are present housings 16 for the framework 17 configured to support the accelerometer 11, the gyroscope 12 and the magnetic sensor 13a of the magnetometer 13, the latter also comprising a permanent magnet 13b associated to the gripper 14 and configured to cooperate with the magnetic sensor 13a when the operator activates the gripper 14.

The latter comprises a pair of manoeuvre levers 22, 23 which are arranged laterally on opposite sides of the handpiece 3 and each of them has an end connected to the casing 15 through a rotation pin 24, 25 to which there are associated elastic means 26, 27.

Each lever 22, 23 has the free opposite end arranged at the disposal of the operator for the activation of the gripper 14.

For such purpose, it should be observed that the levers 22, 23 of the gripper 14 are rotatably coupled to each other through two toothed sectors 28, 29, each of which belongs to one of the aforementioned levers 22, 23 and it is coupled externally to the respective rotation pin 24, 25.

Figure 6:
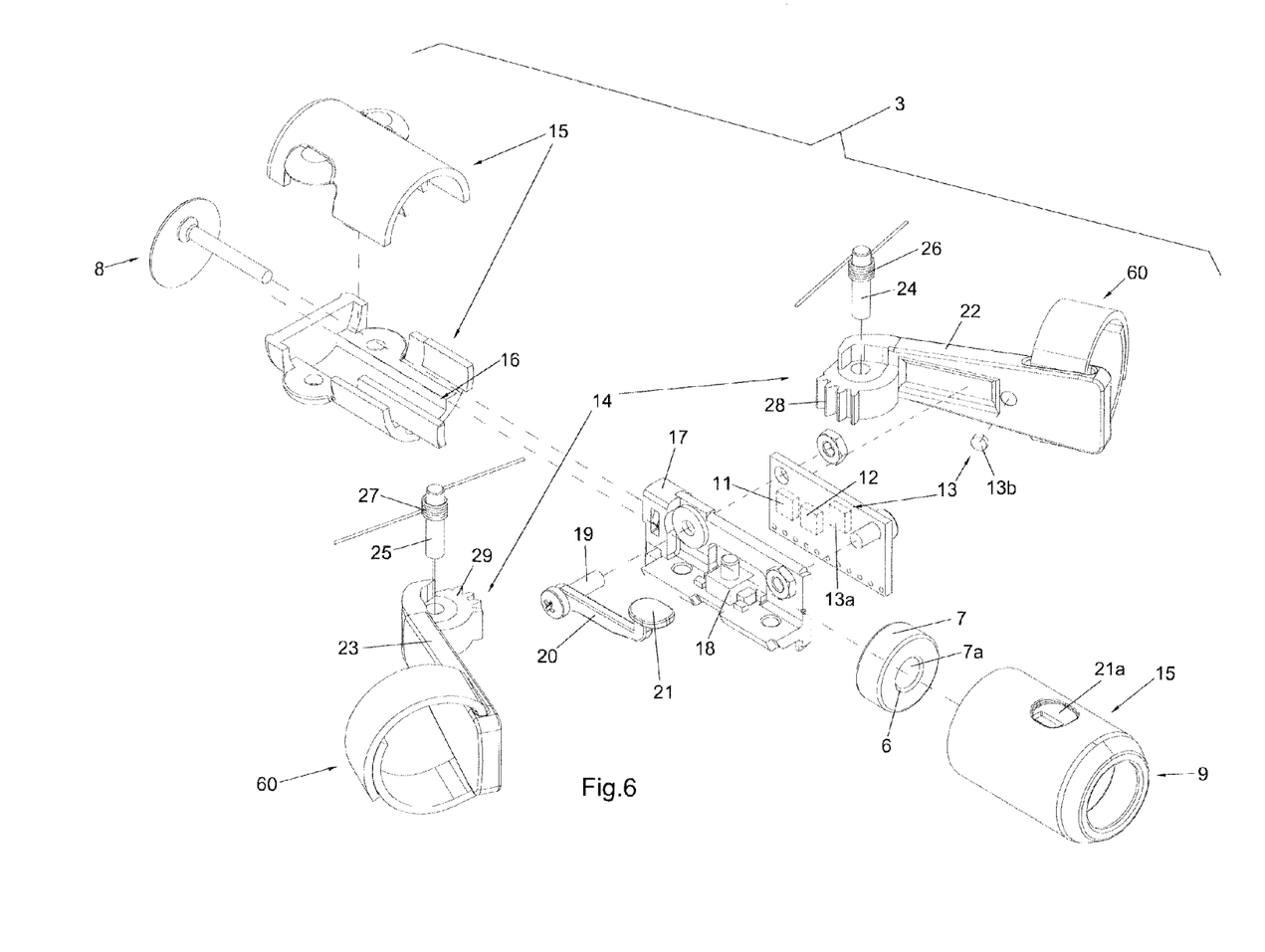
FIG. 6 represents an enlarged and exploded axonometric view of a detail represented in FIGS. 1 and 2.
Figure 7:
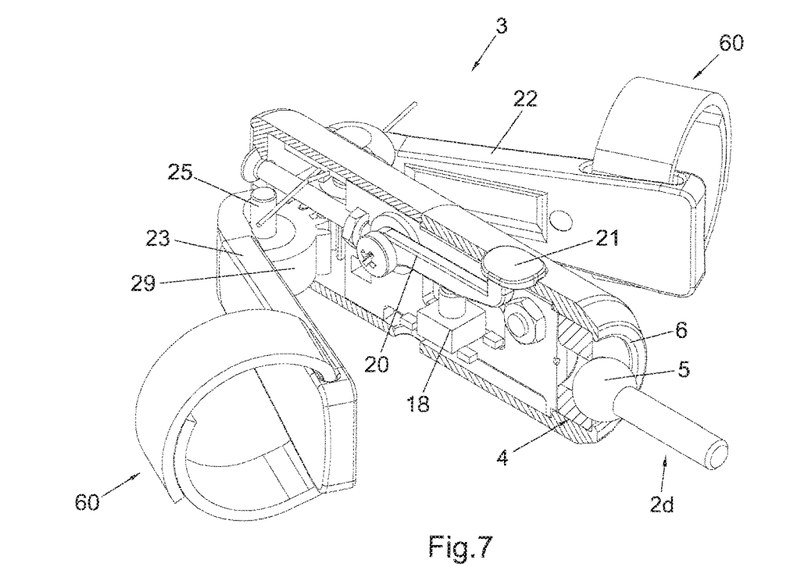
FIG. 7 represents an sectional axonometric view of the detail of FIG. 6 assembled.
Figure 8:
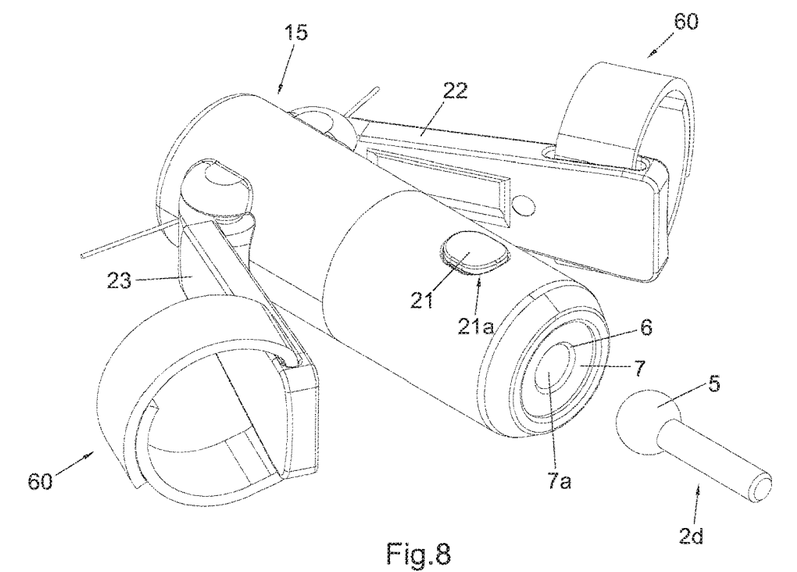
FIG. 8 represents an axonometric view of the detail of FIG. 6 assembled.

To one of the aforementioned levers, for example lever 22 which is observed in FIG. 6, there is associated the magnet 13b which cooperates with the magnetic sensor 13a of the magnetometer 13 when the operator, operating on the end of the levers 22, 23, mutually approaches them to activate the magnetometer 13.

Thus, the handpiece 3 takes a further degree of freedom which is measured with the magnetometer 13 associated to the initial platform.

Thus, the device of the invention comprises an overall number of seven degrees of freedom wherein:
the first, the second and the third degree of freedom are constituted by the rotations of the anthropomorphic arm 2 respectively allowed by the first joint 30, the second joint 40 and the third joint 50;
the fourth, the fifth and the sixth degree of freedom are conferred to the handpiece 3 by the spherical joint 4;
the seventh degree of freedom belongs to the same handpiece 3 and it is conferred by the gripper 14 and the magnetometer 13.

A switch 18 and the rotation pin 19 of a rod 20 for controlling the switch 18, which is provided with a manoeuvre button 21 provided for the operator which projects from the modular casing 15 as observable in FIGS. 9 and 10 through a hole 21a are also associated to the framework 17.

By acting on the manoeuvre button 21, the operator, as observable with reference to FIGS. 9 and 10, activates the control rod 20 and intervenes on the switch 18 so as to activate or de-activate it.

The switch 18 may be used for performing various functions, for example for moving the handpiece 3 maintaining the displayed situations fixed on the monitor.

It should be pointed out that in the present description and in the figures it refers to, there are no electrical connections of the handpiece 3 and the parts forming it with the processing unit which equips the simulation device subject of the invention.

Operatively, when the user intends to simulate the use of the instruments, he applies the handpiece 3 to the anthropomorphic arm 2 magnetically connecting the spherical seat 6 of the latter to the spherical head 5 of the terminal section 2d of the anthropomorphic arm 2.

By holding the handpiece 3 grasped and after inserting the fingers in the Velcro rings 60 which secure it to the levers 22, 23 for manoeuvring the gripper 14, the operator moves the handpiece 3 at the front part of the monitor simulating the use of a remote manipulation instrument.

During the manoeuvre, he utilises the six degrees of freedom allowed by the anthropomorphic arm 2 thus activating the accelerometer 11 and the gyroscope 12, as well as the seventh degree of freedom allowed by the activation of the magnetometer 13 intervening on the gripper 14.

When the operator is required to replace the handpiece 3 with another one configured to simulate a different instrument, it is sufficient to impart to the handpiece 3 such a traction to overcome the magnetic attraction which constrains it to the spherical head 5 of the terminal section 2d of the anthropomorphic arm 2.

Upon separating the handpiece 3 the latter can be substituted by another handpiece configured for simulating a different instrument.

All this occurs very quickly, contrary to what occurs when using similar devices of the prior art.

In addition, the coupling between the spherical head 5 and the spherical seat 6 which make the magnetic spherical joint 4, due to the particular configuration which was described and which is represented in the FIGS. 9 and 10, allows rotating the handpiece 3 with respect to the terminal section 2d of the anthropomorphic arm 2 by a solid angle whose width may reach the value π and even exceed it at times.

Lastly, the housing of the magnetometer, the accelerometer and the gyroscope in the handpiece instead of the joint, which simulates the wrist which connects it to the anthropomorphic arm, simplifies the construction of the device in its entirety.

According to the information above, it is clear that the device of the invention attains all the preset objects.

In particular, the magnetic coupling spherical joint which connects the handpiece to the anthropomorphic arm allows quick mounting and demounting of the handpiece without having to perform mounting and demounting operations of the spherical joint which were instead required in simulation devices of the known type.

In addition, the particular configuration of the spherical joint made up of the spherical head which is coupled in the spherical seat of the demagnetised annular body allows the rotation of the handpiece with respect to the terminal section of the anthropomorphic arm which is connected according to solid rotation angles having width equivalent or even greater than the value π.

In the execution step, the device of the invention may be subjected to modifications and variants which, though not represented and described, should they fall in the contents of the claims below, shall be deemed within the scope of protection of the present invention.

Should the technical characteristics indicated in the claims be followed by reference signs, the latter are indicated solely with the aim of increasing the intelligibility of the claims and, thus, such reference signs shall have no limiting effect on the scope of protection of each element identified by them by way of example.

The invention claimed is:

1. A multidimensional input device comprising an anthropomorphic arm with a handpiece which can be grasped by an operator configured to interact with a scenario represented in a display unit, said handpiece being removably associable to a terminal section of said anthropomorphic arm through a magnetic coupling spherical joint, wherein the handpiece comprises:
    an inertial platform comprising an accelerometer, a gyroscope and a magnetometer;
    a gripper provided for the operator.

2. The device according to claim 1, wherein said spherical joint comprises a spherical head belonging to said terminal section of said anthropomorphic arm or said handpiece, said spherical head being configured to be removably coupled to a corresponding spherical seat belonging to said handpiece or to said terminal section of said anthropomorphic arm, said spherical head and/or said spherical seat being magnetised.

3. The device according to claim 2, wherein said spherical seat belongs to an annular body associated to said handpiece in which said spherical seat is the perimeter edge which delimits the through hole present in said annular body.

4. The device according to claim 3, wherein said handpiece comprises:
    a first end configured to be faced towards an operator who grasps said handpiece;
    a second end configured to receive said annular body.

5. The device according to claim 4, wherein said handpiece is defined by a modular casing in which there is present a framework configured to house:
    said accelerometer, said gyroscope and the magnetic sensor of said magnetometer, said magnetometer also comprising a permanent magnet associated to said gripper which cooperates with said magnetic sensor when the operator activates said gripper;
    a switch;
    the rotation pin of a control rod of said switch provided with a manoeuvre button which projects from said modular casing.

6. The device according to claim 5, wherein said gripper comprises a pair of levers arranged laterally and on opposite sides of said handpiece, each of said levers having an end connected to said casing through a rotation pin provided with elastic means and the free opposite end and provided for the operator for the activation of said gripper.

7. The device according to claim 6, wherein said levers are rotatably coupled to each other through toothed sectors each of which belongs to one of said levers and it is coupled externally to the respective rotation pin.

8. The device according to claim 7, wherein said anthropomorphic arm comprises:
    a first section associated to a support structure through a first joint configured to define a first rotation axis (Z);
    a second section associated to said first section through a second joint configured to define a second rotation axis (Y);
    a third section associated to said second section through a third joint configured to define a third rotation axis (X);
    a terminal section having an end configured to be associated to said third section and the opposite end associated to said handpiece through said spherical joint.

9. The device according to claim 8, wherein said handpiece has seven degrees of freedom which comprise:
    a first degree of freedom defined by the rotation of said first section according to said first rotation axis (Z);
    a second degree of freedom defined by the rotation of said second section according to said second rotation axis (Y);
    a third degree of freedom defined by the rotation of said third section according to said third rotation axis (X);
    a fourth, a fifth and a sixth degree of freedom defined by the rotation of said spherical joint;
    a seventh degree of freedom defined by the mutual movement of approaching and moving away said levers which define said gripper.

* * * * *